United States Patent [19]
Atsuchi et al.

[11] Patent Number: 5,843,909
[45] Date of Patent: Dec. 1, 1998

[54] (3-β), 4-α, 16-β)-16, -23, 28-TRIHDROXYOLEAN-12-ENE-3-YL-β-D-GLUCOPYRANURONIC ACID DERIVATIVES, AS GLUCOSE ABSORPTION INHIBITING AGENTS

[75] Inventors: Mikito Atsuchi; Yuri Hirao; Yoshio Iwasaki, all of Tokyo, Japan

[73] Assignee: Kowa Chemical Industries Co., Ltd., Osaka, Japan

[21] Appl. No.: 874,675

[22] Filed: Jun. 13, 1997

[51] Int. Cl.$^6$ .............................. A61K 31/70; C07H 15/24
[52] U.S. Cl. ................................ 514/27; 536/4.1
[58] Field of Search ...................... 536/5, 4.1; 514/26, 514/27

[56] References Cited
PUBLICATIONS

Atsuji et al CA 125:257167; JP 08208689A2, Aug. 6, 1996.

*Primary Examiner*—Gary L. Kunz
*Attorney, Agent, or Firm*—Medlen & Carroll, LLP

[57] ABSTRACT

The present invention relates to (3β, 4α,16β)-16,23,28-trihydroxyolean-12-ene-3-yl-β-D-glucopyranuronic acid derivatives and a method for preparing the same from *Gymnema inodorum* leaves, which comprises treating *Gymnema inodorum* leaves with an aqueous acid solution, extracting the leaves with an alcohol and/or water, concentrating the extract and subjecting to liquid-liquid partition extraction with water and 1-butanol, concentrating and drying/caking the 1-butanol phase under reduced pressure, defatting the cake, extracting soluble components from the cake with a high polar solvent, concentrating and drying/caking the extract to obtain a purified *Gymnema inodorum* leaf extract, and then applying the purified extract to HPLC to obtain fractions containing glucose absorption inhibiting substances.

9 Claims, 7 Drawing Sheets

(3-β), 4-α, 16-β)-16, -23, 28-TRIHDROXYOLEAN-12-ENE-3-YL-β-D-GLUCOPYRANURONIC ACID DERIVATIVES, AS GLUCOSE ABSORPTION INHIBITING AGENTS

BACKGROUND OF THE INVENTION

1. Field of the Invention

The present invention relates to (3β, 4α, 16β)-16,23,28-trihydroxyolean-12-ene-3-yl-β-D-glucopyranuronic acid derivatives which are novel compounds represented by the general formula (I):

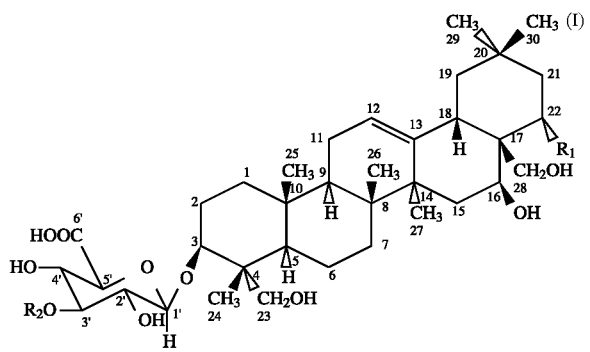

wherein $R_1$ is a hydrogen atom or a group represented by the following formula:

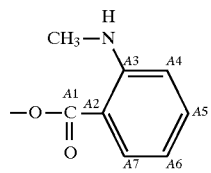

and $R_2$ is a hydrogen atom or a group represented by the following formula:

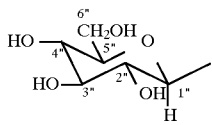

The present invention also relates to a method for preparing the compound represented by the general formula (I) above, in particular, from an extract of *Gymnema inodorum* leaves.

The present invention further relates to a glucose absorption inhibiting agent comprising at least one compound represented by the general formula (I) above, and a food or drink additive comprising at least one compound represented by the general formula (I) above.

The present invention further relates to a dietary food or drink, or a diabetes-preventive food or drink comprising at least one compound represented by the general formula (I) above.

2. Description of the Prior Art

Recently, the coming of a highly aged society and an increase in patients with adult diseases have become problems. With respect to diabetes, it is said that there are 5–6 millions of patients in Japan including potential patients with hyperglycemia. Non-insulin-dependent diabetes mellitus (NIDDM), pregnancy diabetes mellitus (GDM) and the like which are particularly high in incidence among various diabetes are considered to be caused mainly by overeating and corpulence (fatness). In particular, excessive intake of saccharides (such as sugar and starch) whose major component is glucose readily absorbed in intestinal tracts is said undesirable, because such excessive intake results in corpulence and puts a heavy burden upon β cells secreting insulin to thereby cause abnormalities in glucose tolerance. Therefore, it is desirable to prevent excessive intake of those saccharides. However, appetite for food is one of human desires and it is extremely difficult to control one's appetite at present in the so-called "age of satiation". Under such circumstances, recently, there has been a growing interest in digestive enzyme inhibiting agents which inhibit the digestion of sugar and starch, and glucose absorption inhibiting agents which inhibit the absorption of glucose generated by digestion.

As glucose absorption inhibiting substances, there have been known phloridzin, zizyphine and gymnemic acid, etc. which are saponins. However, phloridzin has an adverse effect that it induces renal glucosuria and, thus, it is not preferable as an additive to food or drink. On the other hand, zizyphine and gymnemic acid greatly spoil the inherent flavor of food or drink because of their sweet taste suppressing action, which can be said a fatal problem for them to be used widely as an additive to food or drink.

The present inventors have previously found that leaves of a liana, *Gymnema inodorum*, growing wild in Southeast Asia broadly do not have astringency, bitterness nor gustation modifying action such as suppression of sweetness, and yet have an action to inhibit glucose absorption in intestinal tracts. Then, the inventors have proposed a tea obtained by drying and roasting leaves of the above-mentioned plant, a dark-brown, unpurified *Gymnema inodorum* leaf extract obtained by extracting leaves of the plant with hydrous alcohol or water, and food and drink obtained by adding thereto the tea or the extract (Japanese Unexamined Patent Publication No. 3-172156).

The previously proposed *Gymnema inodorum* leaf extract as described above has a relatively moderate glucose absorption inhibiting action. Therefore, a relatively large amount of the extract should be added to food or drink. Since the extract has a dark brown color, the food or drink to which the extract has been added tends to be colored brown although the food or drink does not have astringency, bitterness nor gustation modifying action such as suppression of sweetness. When the food or drink originally has a light color, the addition of the above extract remarkably spoils the inherent color and thus is undesirable.

In addition, during the processing of the food or drink to which the extract has been added, there has been a danger that components having the glucose absorption inhibiting action undergo degradation by heat, light and chemical substances such as acid and alkali and lose the glucose absorption inhibiting action which is the object of the food or drink. However, there has been no simple method to confirm that the food or drink retains the the glucose absorption inhibiting action except carrying out an effect test for each lot of the food or drink. In other words, it has been necessary to decolor and purify *Gymnema inodorum* extract so that it would not spoil the inherent color of a food or drink when added thereto. Further, it has been required to establish a quality control method by high performance liquid chromatography (HPLC) or the like to identify and quantitatively determine the glucose absorption inhibiting action in a food or drink to which *Gymnema inodorum* roasted tea or leaf extract has been added. For this purpose, it has been necessary to identify and isolate/purify the glucose absorption inhibiting substance of interest from components of *Gymnema inodorum* leaves.

OBJECTS AND SUMMARY OF THE INVENTION

It is an object of the present invention to provide substances having glucose absorption inhibiting action; a method for preparing the substances from *Gymnema inodorum* leaves; a glucose absorption inhibiting agent comprising the substance(s); a food or drink additive comprising the substance(s); a dietary food or drink comprising the substance(s); and a diabetes-preventive food or drink comprising the substance(s).

The present inventors considered that the glucose absorption inhibiting substance contained in *Gymnema inodorum* leaves should be a species of saponin like gymnemic acid. Based on conventional extraction, separation and preparation methods for saponins, the inventors have make extensive and intensive researched and finally succeeded in isolating and purifying four glucose absorption inhibiting substances from *Gymnema inodorum* leaves. Briefly, the inventors have confirmed that those glucose absorption inhibiting substances are present in crude fraction II in the preparative HPLC chart shown in FIG. 1., and that those substances are the components of peaks 1, 4, 6 and 7, respectively, contained in crude fraction II. Further, it has been found that those glucose absorption inhibiting substances are able to inhibit the absorption of glucose in intestinal tracts effectively even in an extremely small amount.

As a result of further researches on the above-mentioned four substances having glucose absorption inhibiting action, it has been found that these substances are novel compounds which have never been described in the literature and have chemical structures as represented by the general formula (I) below. Therefore, the present invention relates to (3β, 4α, 16β)-16,23,28-trihydroxyolean-12-ene-3-yl-β-D-glucopyranuronic acid derivatives represented by the general formula (I):

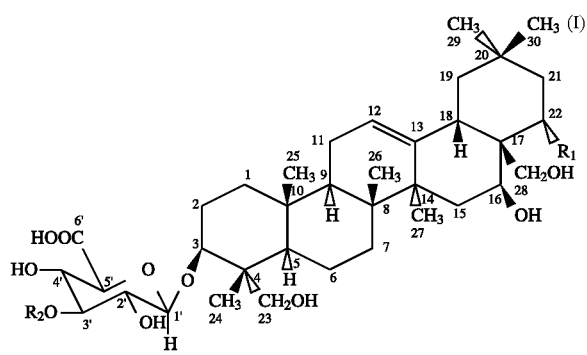

wherein $R_1$ is a hydrogen atom or a group represented by the following formula:

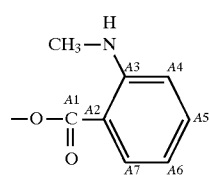

and $R_2$ is a hydrogen atom or a group represented by the following formula:

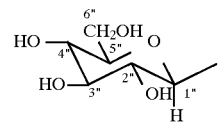

The present invention relates to (3β, 4α, 16β)-16,23,28-trihydroxyolean-12-ene-3-yl-β-D-glucopyranuronic acid represented by the formula (I) wherein both $R_1$ and $R_2$ are a hydrogen.

The present invention relates to (3β, 4α, 16β, 22α)-22-(N-methylanthraniloxy)-16,23,28-trihydroxyolean-12-ene-3-yl-3-O-β-D-glucopyranosyl-β-D-glucopyranuronic acid represented by the formula (I) wherein $R_1$ is a group represented by the following formula:

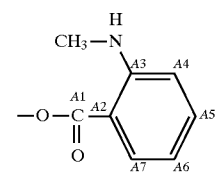

and $R_2$ is a group represented by the following formula:

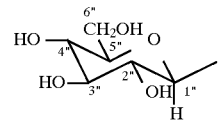

The present invention relates to (3β, 4α, 16β, 22α)-22-(N-methylanthraniloxy)-16,23,28-trihydroxyolean-12-ene-3-yl-β-D-glucopyranuronic acid represented by the general formula (I) wherein $R_1$ is a hydrogen and $R_2$ is a group represented by the following formula:

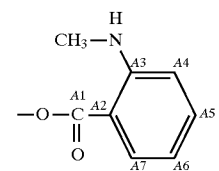

The present invention also relates to a method for preparing, as glucose absorption inhibiting substances contained in *Gymnema inodorum* leaves, the substances of peaks 1, 4, 6 and 7 contained in crude fraction II shown in FIG. 1. Further, the invention relates to a method for obtaining a colorless or light yellow mixture of glucose absorption inhibiting substances containing one to four of the above four substances. The method comprises:

treating *Gymnema inodorum* leaves with an aqueous acid solution;
dehydrating and washing the leaves;
drying the leaves;
extracting the leaves with methanol, hydrous methanol, hydrous ethanol or water;
concentrating the resultant extract under reduced pressure;
subjecting the resultant concentrate to a liquid-liquid partition extraction with water and 1-butanol;
adding diatomaceous earth or the like to the resultant 1-butanol phase and then concentrating and drying/caking the phase under reduced pressure;
then washing the resultant cake with an organic solvent to defat the cake;

extracting the resultant cake with a highly polar solvent such as methanol;

filtering the resultant extract and concentrating and drying/caking the filtrate under reduced pressure to thereby obtain a light green, purified *Gymnema inodorum* leaf extract; and subjecting the resultant extract to a preparative HPLC of a reversed phase partition system using as a stationary phase an octadecyl group-bound silica gel under the following conditions:

[Conditions in preparative HPLC]
Preparative column:
TSKgel ODS-80T$_M$ (reversed-phase partition system/Tosoh Corp.)
Column size: 21.5 mm I.D.×30 cm
Eluent:
Solution A Acetonitrile:distilled water:acetic acid =50.0:50.0:0.1 (v/v%)
Solution B Acetonitrile:distilled water:acetic acid =55.2:44.8:0.1 (v/v%)
Solution C Acetonitrile:distilled water:acetic acid =90.0:10.0:0.1 (v/v%)
Gradient:
0→78 min. A→B linear gradient
78→83 min. B→C linear gradient
83→140 min. isocratic elution with Solution C
Flow rate:
6.0 ml/min.
Detector:
Ultraviolet-visible detector (210 nm)
Column temperature:
40° C.
Glucose absorption inhibiting substances:
31.5–33.5 min.: peak 1 component
53.0–58.5 min.: peak 4 component
67.5–73.0 min.: peak 6 component
77.0–81.5 min.: peak 7 component
Glucose absorption inhibiting mixture:
31.5 min.≦preparative time≦81.5 min.: crude fraction II Further, the present invention relates to a glucose absorption inhibiting agent comprising at least one (3β, 4α, 16β)-16,23,28-trihydroxyolean-12-ene-3-yl-β-D-glucopyranuronic acid derivative represented by the general formula (I) above.

The present invention also relates to a food or drink additive comprising at least one (3β, 4α, 16β)-16,23,28-trihydroxyolean-12-ene-3-yl-β-D-glucopyranuronic acid derivative represented by the general formula (I) above.

The present invention relates to a dietary food or drink comprising at least one (3β, 4α, 16β)-16,23,28-trihydroxyolean-12-ene-3-yl-β-D-glucopyranuronic acid derivative represented by the general formula (I) above.

The present invention further relates to a diabetes-preventive food or drink comprising at least one (3β,4α,16β)-16,23,28-trihydroxyolean-12-ene-3-yl-β-D-glucopyranuronic acid derivative represented by the general formula (I) above.

DETAILED DESCRIPTION OF THE INVENTION

Figure 1:
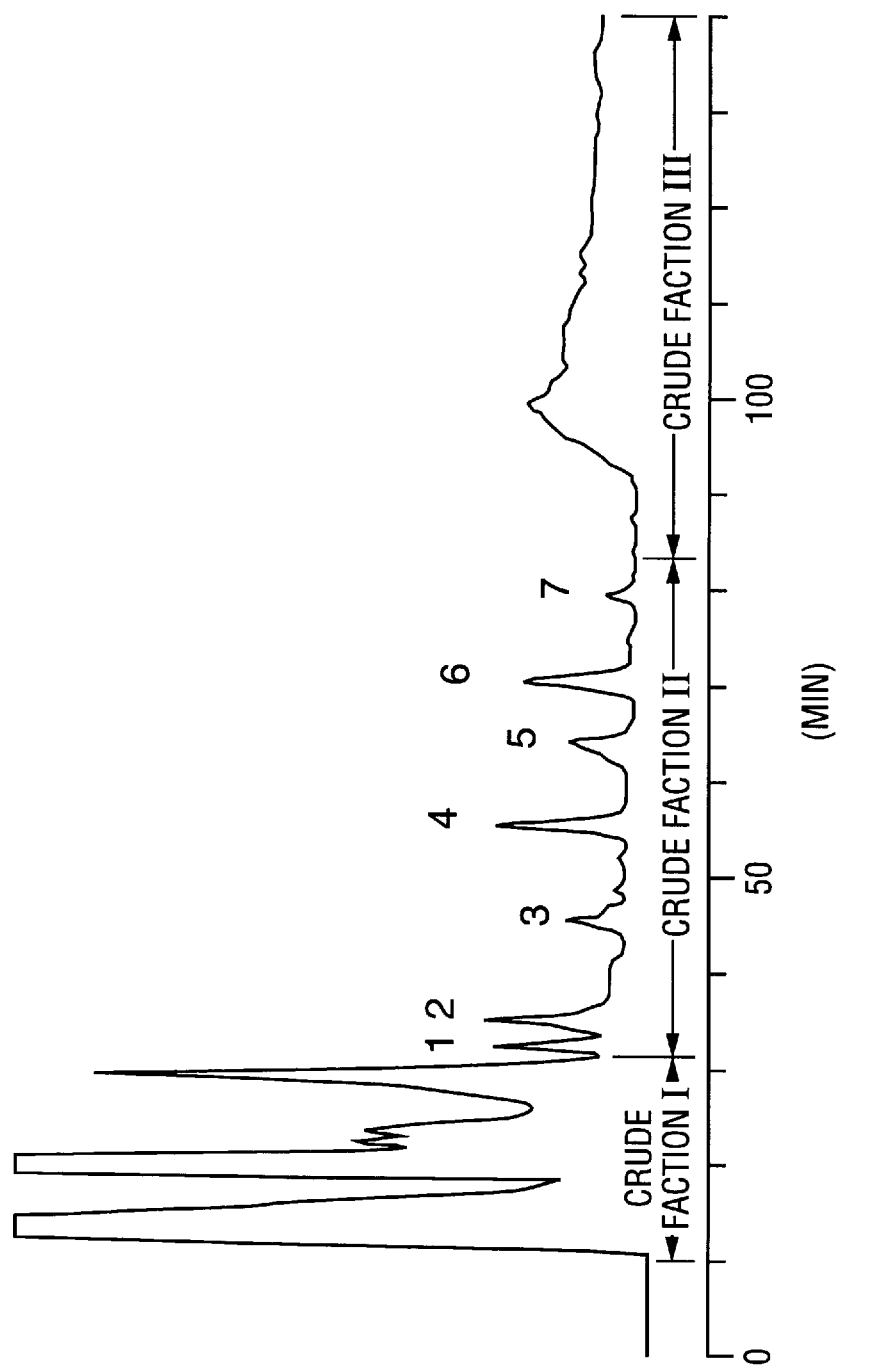
FIG. 1 is a preparative HPLC chart of peak 1, peak 4, peak 6 and peak 7 components in crude fraction II in Example 1.

Hereinbelow, a method for preparing the compound of the invention represented by the general formula (I) above will be described in detail.

Pretreatment/Decoloring Step with an Acid Solution

This step aims at removing in advance water-soluble saccharides, amino acids, basic pigments etc. which are contained abundantly in *Gymnema inodorum* leaves. This step is carried out in order to perform the subsequent decoloring step and liquid—liquid partition extraction step smoothly. Examples of acids which may be used in this step includes ascorbic acid, chloric acid, citric acid, gluconic acid, succinic acid, acetic acid, tartaric acid, lactic acid, sulfuric acid, malic acid and phosphoric acid. For foods and drinks, souring agents such as ascorbic acid, citric acid, gluconic acid, succinic acid, acetic acid, tartaric acid, lactic acid and malic acid are preferable. The pH range of the acid solution is preferably 2–3.

The volume of the acid solution is preferably 0.5–10 liters per 100 g of *Gymnema inodorum* dried leaves. The treatment temperature is preferably from room temperature to 40° C.

The treatment time is preferably 0.5–2 hours and it is preferred to repeat the treatment 1–4 time. As to the treatment equipment, usually, an agitator is used. For the dehydration/separation of the treated leaves, usually, a centrifugal dehydrator is used. At the final step of the dehydration, remaining acid is washed and removed using 0.5–2 liters of water per 100 g of dried leaves.

Extraction Step

As an extraction solvent to be used in the extraction step for the acid-treated leaves, conventional solvents such as methanol, hydrous methanol, hydrous ethanol, or water may be enumerated. For foods and drinks, hydrous ethanol is preferable, of which the moisture content is 10–80%, preferably 20–60%. The extraction ratio is 0.5–10 liters, preferably 0.5–2 liters of the extraction solvent to 100 g of the acid-treated leaves. The extraction temperature is preferably from room temperature to 80° C. The extraction time is preferably 0.5–6 hours. The extraction is repeated preferably 214 4 times. As to the extraction equipment, usually, an agitator is used and an extract is obtained through conventional filtering equipment.

Concentration Step

This step aims at a prompt shift to the subsequent partition extraction step. When the extraction solvent was methanol, 0.5–1 liter of water is added to 100 g of the acid-treated leaves and then concentrated under reduced pressure until the smell of methanol has been eliminated. When the extraction solvent was hydrous ethanol, the extract is concentrated under reduced pressure until the the smell of ethanol has been eliminated and the concentrate has become 0.5–1 liter per 100 g of the acid-treated leaves. When the extraction solvent was water, the extract is concentrated under reduced pressure until the concentrate has become 0.5–1 liter per 100 g of the acid-treated leaves. As to the concentration equipment, usually, a rotary evaporator or a thin-membrane slash evaporator is used.

Partition Extraction Step

This step aims at separating and purifying saponins from the mixture by utilizing the difference in partition coefficient between the two liquid phases of water and 1-butanol. It is one of effective conventional methods. Usually, a preferable mixing ratio is 0.5–1 liter of the concentrate and 0.25–1 liter of 1-butanol per 100 g of the initial, acid-treated leaves. The shaking time is preferably 5–30 minutes. The partition extraction is repeated preferably 1–3 times. As to the partition extraction instrument and equipment, usually, a separating funnel and a shaker are used.

Defatting/Decoloring Step

This step aims at removing lipids and lipid-soluble pigments by adding an excipient, such as diatomaceous earth, to the 1-butanol phase obtained by the partition extraction, concentrating and drying/caking the resultant phase under reduced pressure, crushing the resultant cake, extracting the crushed material with an organic solvent such as diethyl ether and filtering the extract. As the excipient, celite, silica gel, active carbon and the like may be enumerated in addition to diatomaceous earth. The amount of the excipient to be added is preferably 10–100 g per 100 g of the initial, acid-treated leaves. As the defatting solvent, petroleum ether, n-hexane, benzene, chloroform, ethyl acetate and the like may be enumerated in addition to diethyl ether. In terms of the decoloring effect, diethyl ether and ethyl acetate are preferable. The amount of this solvent is preferably 0.25–1 liter per 100 g of the initial, acid-treated leaves. The defatting temperature is preferably 0°–40° C. The defatting time is preferably 5–60 minutes. The defatting is repeated preferably 2–4 times. As to the concentration equipment, usually, a rotary evaporator or the like is used. As to the defatting equipment, usually, an agitator is used, but an ultrasonic cleaner or the like may be used if the material to be treated is small.

Purification with a Highly Polar Solvent

This step aims at obtaining a purified *Gymnema inodorum* leaf extract of light yellowish green which contains at relatively high concentrations the glucose absorption inhibiting substances of interest adsorbed on the excipient such as diatomaceous earth. As a highly polar solvent, acetone, ethanol, tetrahydrofuran and the like may be enumerated in addition to methanol. The amount of this solvent is preferably 0.1–1 liter per 100 g of the initial, acid-treated leaves. The treatment temperature is preferably from room temperature to 40° C. The treatment time is preferably 5–60 minutes. This treatment is repeated preferably 2–4 times. As to the treating equipment, usually, an agitator is used, but an ultrasonic cleaner or the like may be used if the material to be treated is small. As to the concentrating/drying/caking equipment, usually a rotary evaporator or the like is used.

Isolation and Purification by Preparative HPLC

The purified *Gymnema inodorum* leaf extract is dissolved in an aqueous solution of 50% ethanol using 10 ml of the solution per 1 g of the extract. The resultant solution is filtered and again filtered through a disposable filter 0.45 $\mu$m in pore size. The filtrate is subjected to preparative HPLC to thereby obtain the fractions from 31.5–33.5 min., 53.0–58.5 min., 67.5–73.0 min. and 77.0–81.5 min. which are the glucose absorption inhibiting substances. Further, a glucose absorption inhibiting mixture is obtained from crude fraction II falling within in any range of 31.5 min.$\leq$preparative time$\leq$81.5 min. containing 1–4 of the above-mentioned four glucose absorption inhibiting substances.

The preparative conditions in the preparative HPLC are as follows:

Preparative column:
TSKgel ODS-80 $T_M$ (reversed-phase partition system/Tosoh Corp.)

Column size:
21.5 mm I.D.×30 cm

Eluent:
Solution A Acetonitrile:distilled water:acetic acid =50.0:50.0:0.1 (v/v%)

Solution B Acetonitrile:distilled water:acetic acid =55.2:44.8:0.1 (v/v%)

Solution C Acetonitrile:distilled water:acetic acid =90.0:10.0:0.1 (v/v%)

Gradient:
0→78 min. A→B linear gradient
78→83 min. B→C linear gradient
83→140 min. isocratic elution with Solution C Flow rate:
6.0 ml/min.

Detector:
Ultraviolet-visible detector (210 nm)

Column temperature:
40° C.

Glucose absorption inhibiting substances:
31.5–33.5 min.: peak 1 component
53.0–58.5 min.: peak 4 component
67.5–73.0 min.: peak 6 component
77.0–81.5 min.: peak 7 component Glucose absorption inhibiting mixture:
31.5 min.$\leq$preparative time$\leq$81.5 min.: crude fraction II Preparative chart:
see FIG. 1.

The thus obtained each fraction solution is concentrated under reduced pressure and acetonitrile is removed. The concentrate is subjected to liquid—liquid partition extraction using 1-butanol. The resultant 1-butanol phase is concentrated and dried/caked under reduced pressure to thereby obtain each fraction.

Recrystallization

The thus obtained each fraction is dissolved in a diethyl carbonate solution containing 10% methanol, filtered and left at room temperature. The colorless or light yellow crystals deposited are separated by filtration and vacuum dried to thereby obtain the glucose absorption inhibiting substances of interest and a mixture containing those substances. As to the recrystallization solvent, it is preferable to use a highly polar solvent having a relatively low boiling point (such as acetone, ethanol, tetrahydrofuran and methanol) in combination with a slightly polar solvent having a relatively high boiling point (such as o-xylene, chloroform, cyclohexane, toluene, n-hexane, benzene and diether carbonate). Preferably, 5–50 ml of a highly polar solvent and 20–500 ml of a slightly polar solvent are used per 1 g of the concentrated and dried/caked material.

Additionally, the properties of the peak 1, peak 4, peak 6 and peak 7 components were determined using the following equipment and measuring conditions. As a result, the chemical structure of a substance which constitutes each of the above components has been determined.

(Melting Point)
Equipment: Yanagimoto Micro-Melting Point Measuring Equipment MP-500D (UV)
Equipment: Tosoh Corp. UV8010
Data processing: Tosoh Corp. SC8010 spectrum measurement mode
Wave length observed: 195–369 nm
Solvent: 50% $CH_3CN$ solution
Concentration: 100–500 ppm
Temperature: 25° C.

(IR)
Equipment: Shimadzu IR-400
Measuring method: KBr tablet method (MS)
Equipment: VG Co. ZAB-HF mass spectrometer
Data processing: VG Co. 11/250 data processing system
Ionization method: FAB
Ions measured: anions
Bombardment atom: xenon
Bombardment atom acceleration voltage: approx. 8 kV
FAB gun emission current: approx. 1 mA
Matrix: diethanolamine
Ion acceleration voltage: 8.0 kV
Scanning rate: 30 sec./decade
scanning range: m/z 10–1500
Scanning interval: 2 sec.

(NMR)
Equipment: JOEL JNM-GSX 500
Frequency observed: $^1H$; 500.2 MHz, $^{13}C$; 125.8 MHz
Solvent: $CD_3OD$
Concentration: approx. 20 mg/600 μl
Standard: $^1H$; TMS, $^{13}C$; $CD_3$=49.0 ppm
Temperature: 30° C.

As a result of the above measurements, the components described above have been found to be the following substances:

(1) Peak 1 Component (fraction: 31.5–33.5 min.)

(3β,4α, 16β)-16,23,28-trihydroxyolean-12-ene-3-yl-β-D-glucopyranuronic acid. m.p.: 203°–206° C. Molecular weight: 650.

(2) Peak 4 Component (fraction: 53.0–58.5 min.)
(3β, 4α, 16β, 22α)-22-(N-methylanthraniloxy)-16,23,28-trihydroxyolean-12-ene-3-yl-3-O-β-D-glucopyranosyl-β-D-glucopyranuronic acid. m.p.: 218°–221° C. Molecular weight: 961.

(3) Peak 6 Component (fraction: 67.5–73.0 min.)
(3β, 4α, 16β, 22α)-22-(N-methylanthraniloxy)-16,23,28-trihydroxyolean-12-ene-3-yl-β-D-glucopyranuronic acid. m.p.: 213–216° C. Molecular weight: 799.

(4) Peak 7 Component (fraction : 77.0–81.5 min.)
Chemical structure is unknown. m.p.: 219°–221° C.

Each of the glucose absorption inhibiting substances and the glucose absorption inhibiting mixture of the invention comprising the above-described component(s) are relatively readily-soluble in highly polar solvents such as acetone, ethanol, hydrous ethanol, tetrahydrofuran and methanol, fairly soluble in water, and sparingly soluble in slightly polar solvents such as o-xylene, chloroform, cyclohexane, toluene, n-hexane and benzene.

The glucose absorption inhibiting substances and the glucose absorption inhibiting mixture of the invention are able to inhibit the glucose absorption in intestinal tracts even in an extremely small amount. Therefore, a food or drink to which the above substance or mixture of the invention has been added or which contains the substance or mixture inhibits the absorption of the glucose generated from digestion of sucrose, starch, etc. contained in the above food or drink and other food or drink taken almost simultaneously, while maintaining the inherent color of the food or drink. Thus, such a food or drink is expected to inhibit excessive energy intake and thereby to prevent corpulence as well as non-insulin-dependent diabetes mellitus (NIDDM) and pregnancy diabetes mellitus (GDM) of which the major cause is corpulence. Therefore, the glucose absorption inhibiting substances and the glucose absorption inhibiting mixture of the invention are preferable as raw materials for food or drink additives, dietary foods or drinks and diabetes-preventive foods or drinks.

The amount of the glucose absorption inhibiting substance or the glucose absorption inhibiting mixture of the invention to be added to a food or drink is 1–100 mg, preferably 5–20 mg per 100 g of a food or drink. When a larger amount than this is added, the effect will be the same and not preferable from economical point of view, though problems of side effects such as hypoglycemia would not occur. The amount of the previously proposed unpurified *Gymnema inodorum* leaf extract to be added is 20–2,000 mg, preferably 100–400 mg per 100 g of a food or drink.

Each of the glucose absorption inhibiting components prepared by the above-described method can be added to various foods and drinks. Examples of foods and drinks which may be used in the present invention include various juices, any sweet stuff such as chocolate and candy, ice cream, noodles, rice, rice cake, sweetening agents, jams, and liquors. Besides these foods and drinks rich in saccharides, the glucose absorption inhibiting substance of the invention may be added to sugar-free drinks or foods (e.g., drinking water, tea, pickles) or seasonings (e.g., soy sauce, soy bean paste, mayonnaise) since the substance of the invention is able to inhibit the absorption of glucose contained in other food or drink taken simultaneously with a food or drink containing the substance of the invention. The food or drink according to the invention can maintain its inherent color because the glucose absorption inhibiting substance(s) and the glucose absorption inhibiting mixture are colorless or light yellow powder.

In addition, because each of the glucose absorption inhibiting substances contained in *Gymnema inodorum* leaves could be isolated as a single component, now it is possible to qualitatively and quantitatively analyze the above component in the food or drink of the invention by HPLC or the like. Thus, it is possible to confirm that the component has not been degraded by heat, light and chemicals such as acid and alkali during its processing steps. The problem of quality control has been solved.

PREFERRED EMBODIMENTS OF THE INVENTION

Hereinbelow, the present invention will be described in more detail with reference to the following Examples, which should not be construed as limiting the scope of the present invention.

EXAMPLE 1
Pretreatment/Decoloring Step with an Acid Solution

Dried *Gymnema inodorum* leaves were crushed into 0.5–2 mm. To 1 kg of the dried crushed leaves, 10 liters of an aqueous citric acid solution (pH 2.5) was added and agitated at room temperature. After 1 hour, the resultant mixture was centrifugally dehydrated continuously at 1,500 G using a 800 mesh filter cloth (PP). Finally, the leaves were washed with 4 liters of water, and then centrifugally dehydrated further. Thereafter, the leaves were dried in a drier at 80° C. for 16 hours to thereby obtain 752 g of acid-treated leaves. Water from the centrifugal dehydration and water from the washing were combined and concentrated to thereby obtain a concentrated residue from acid-treated solution (B).

Extraction Step

To 400 g of the acid-treated leaves, 4 liters of aqueous 50% ethanol solution was added and agitated at room temperature. After 1 hour, the mixture was vacuum filtered using a quantitative filter paper No. 5A (Toyo) to thereby obtain an extract. To the acid-treated leaf cake, 4 liters of aqueous 50% ethanol solution was added again, extracted under agitation for 1 hour at room temperature and then filtered similarly to thereby obtain an extract. Both extracts were mixed to thereby obtain about 8 liters of extract.

Concentration Step

The thus obtained extract was concentrated under reduced pressure in a rotary evaporator under 30 mmHg at 80° C. until the smell of ethanol was eliminated. As a result, 2.2 liters of a concentrate was obtained. Of this concentrate, 200 ml was further concentrated and dried/caked to thereby obtain 4.2 g of light brown, roughly purified *Gymnema inodorum* leaf extract (C). To the remaining 2 liters of the concentrate, water was added to make the total volume 3 liters.

Partition Extraction Step

The thus prepared 3 liter concentrate was divided into six 1 liter separating funnels. To each of these funnels, 300 ml of 1-butanol was added, shaken for 30 minutes using a shaker and then left stationary. About 1.8 liters of 1-butanol solution (E) was obtained by collecting the separated 1-butanol from each funnel. The aqueous phase was concentrated to thereby obtain a concentrated residue from partition aqueous phase (D).

Defatting/Decoloring Step

To the resultant 1-butanol solution, 80 g of diatomaceous earth was added, and then concentrated and dried/caked under 30–5 mmHg at 80° C. using a rotary evaporator. The resultant cake was further dried in a vacuum drier at 80° C. for 16 hours and crushed, to thereby obtain 121.2 g of fine powder of which the excipient was diatomaceous earth. One liter of petroleum ether was added thereto. The mixture was defatted at room temperature for 10 minutes using an ultrasonic cleaner and vacuum filtered with a quantitative filter paper No. 5A (Toyo). The residue was defatted again by the above-mentioned procedures and filtered. The resultant residue was further defatted using 1 liter of ethyl acetate and filtered. The resultant residue was dried in a drier at 80° C. for 1 hour to thereby obtain 105.6 g of fine powder of which the excipient is diatomaceous earth. All of the filtrates obtained from individual filtration steps were collected and concentrated to thereby obtain a concentrated residue from defatted solution (F).

Purification with a Highly Polar Solvent

To the defatted fine powder (105.6 g), 1 liter of methanol was added, treated in an ultrasonic cleaner for 10 minutes at room temperature, and vacuum filtered with a quantitative filter paper No. 5A (Toyo). The residue was treated again by the same procedures as described above and then filtered. Both methanol solutions were mixed together, and then concentrated and dried/caked under 30–5 mmHg at 80° C. using a rotary evaporator. The resultant cake was further dried in a vacuum drier at 80° C. for 16 hours and then crushed, to thereby obtain 22.2 g of light yellow-green, purified *Gymnema inodorum* leaf extract (G).

Isolation and Purification by Preparative HPLC

To 17.4 g of the thus obtained purified *Gymnema inodorum* leaf extract, 174 ml of an aqueous 50% ethanol solution was added and treated in an ultrasonic cleaner at room temperature for 10 minutes. The resultant mixture was filtered with a quantitative filter paper No. 5A (Toyo) and further filtered with a disposable filter 0.45$\mu$m in pore size. The filtrate was applied to preparative HPLC to thereby obtain crude fraction II from 31.5–81.5 min. containing four glucose absorption inhibiting substances. Further, a fraction from 31.5–33.5 min. (peak 1 component), a fraction from 53.0–58.5 min. (peak 4 component), a fraction from 67.5–73.0 min. (peak 6 component), and a fraction from 77.0–81.5 min. (peak 7 component) were obtained which are the above-mentioned four glucose absorption inhibiting substances. Then, each of the fraction solutions obtained by the preparative HPLC was concentrated under reduced pressure using a rotary evaporator under 30 mmHg at 80° C. until the smell of acetonitrile was eliminated.

The resultant concentrate was subjected to liquid-liquid partition extraction using 1-butanol. The 1-butanol phase was concentrated and dried/caked in a rotary evaporator under 30–5 mmHg at 80° C. The resultant cake was further dried in a vacuum drier at 80° C. for 16 hours. Preparative conditions in the preparative HPLC were as follows.

[Conditions in the preparative HPLC]

Preparative column:
  TSKgel ODS-80 $T_M$ (reversed-phase partition system/ Tosoh Corp.)

Column size:
  21.5 mm I.D.×30 cm

Eluent:
  Solution A Acetonitrile:distilled water:acetic acid =50.0:50.0:0.1 (v/v%)
  Solution B Acetonitrile:distilled water:acetic acid =55.2:44.8:0.1 (v/v%)
  Solution C Acetonitrile:distilled water:acetic acid =90.0:10.0:0.1 (v/v%)

Gradient:
  0→78 min. A→B linear gradient

78→83 min. B→C linear gradient
83→140 min. isocratic elution with Solution C
Flow rate:
6.0 ml/min.
Detector:
Ultraviolet-visible detector (210 nm)
Column temperature:
40° C.
Sample concentration:
10% solution
Amount of sample loaded:
1,500 μl/time
Diluent:
aqueous 50% ethanol solution
No. of times of preparation:
Crude fraction II 16 times
Peaks 1, 4, 6 and 7 100 times
Preparative time and yield:
31.5–33.5 min.: peak 1 component 185 mg
53.0–58.5 min.: peak 4 component 80 mg
67.5–73.0 min.: peak 6 component 60 mg
77.0–81.5 min.: peak 7 component 63 mg
31.5–81.5 min.: crude fraction II 510 mg The preparative HPLC fraction chart is given in FIG. 1.

Recrystallization

The thus obtained each fraction was dissolved in 200 volumes of a diethyl carbonate solution containing 10% methanol, filtered and left at room temperature. After several days, deposited crystals were separated by vacuum filtration using Kiriyama Rohto (No. 5A filter paper) and vacuum dried, to thereby obtain colorless or light yellow crystals of each fraction.

The yields of those crystals were as follows.
(Yields after recrystallization)
Peak 1 125 mg
Peak 4 56 mg
Peak 6 44 mg
Peak 7 48 mg
Crude fraction II 298 mg The state of separation and purification of the products from individual steps, each glucose absorption inhibiting substance and the glucose absorption inhibiting mixture obtained in Example 1 were analyzed by analytical HPLC under the following conditions. Also analyzed were other crude fractions and peak components without glucose absorption inhibiting action.

Figure 2:
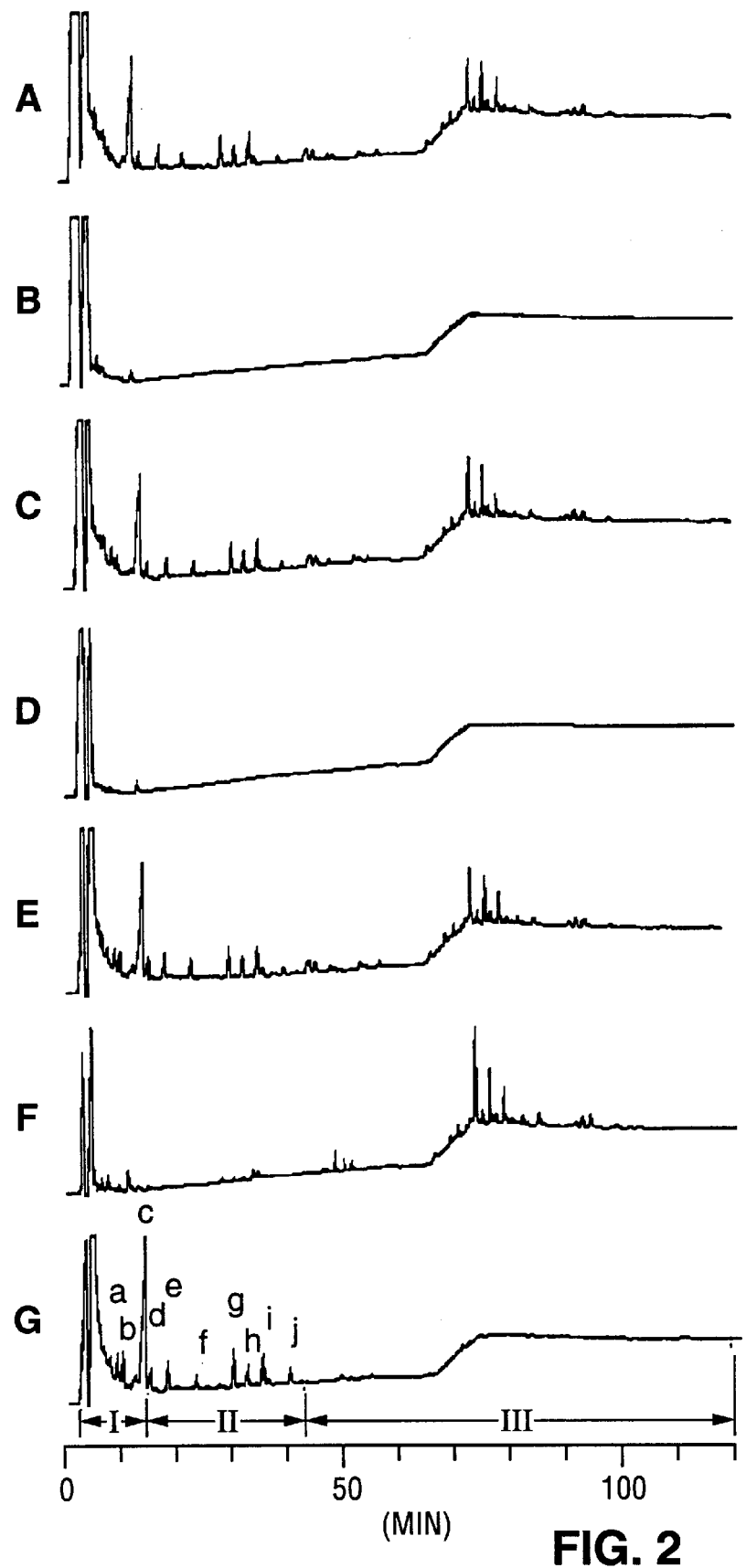
FIG. 2 shows HPLC charts of an unpurified *Gymnema inodorum* leaf extract (A) and the following materials obtained in Example 1: the concentrated residue from acid-treated solution (B); the roughly purified *Gymnema inodorum* leaf extract (C); the concentrated residue from partition aqueous phase (D); the concentrated residue from partition 1-butanol phase (E); the defatted components (F); and the purified *Gymnema inodorum* leaf extract (G).
Figure 3:
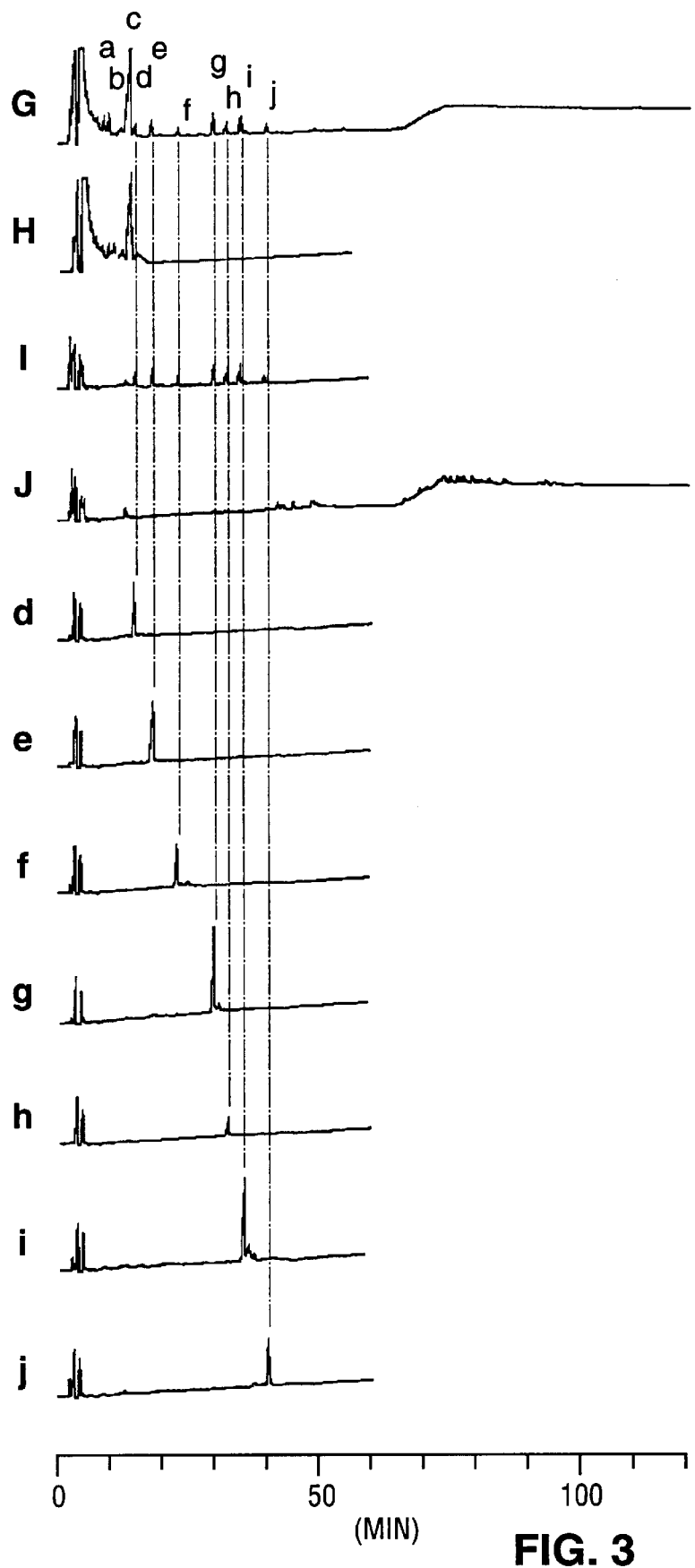
FIG. 3 shows HPLC charts of the following materials obtained in Example 1: the purified *Gymnema inodorum* leaf extract (G); crude fraction I (H); crude fraction II (I); crude fraction III (J); peak 1 component (d); peak 2 component (e); peak 3 component (f); peak 4 component (g); peak 5 component (h); peak 6 component (i); and peak 7 component (j).

(Conditions in the analytical HPLC)
Column:
TSKgel ODS-80 $T_M$ (reversed-phase partition system/ Tosoh Corp.)
Column size:
4.6 mm I.D.×25 cm
Eluent:
Solution A Acetonitrile:distilled water:acetic acid =40.0:60.0:0.1 (v/v%)
Solution B Acetonitrile:distilled water:acetic acid =60.0:40.0:0.1 (v/v%)
Solution C Acetonitrile:distilled water:acetic acid =90.0:10.0:0.1 (v/v%)
Gradient:
0→60 min. A→B linear gradient
60→66 min. B→C linear gradient
66→120 min. isocratic elution with Solution C
Flow rate:
0.8 ml/min.
Detector:
Ultraviolet-visible detector (210 nm)
Column temperature:
40° C.
Amount of sample loaded:
100 μl
Diluent:
A–G: aqueous 50% ethanol solution
H–J, d–j: eluent Solution A
Sample concentration:
A: unpurified *Gymnema inodorum* leaf extract 22.0 mg/ml
B: concentrated residue from acid-treated solution 21.0 mg/ml
C: roughly purified *Gymnema inodorum* leaf extract 10.0 mg/ml
D: concentrated residue from partition aqueous phase 4.0 mg/ml
E: concentrated residue from partition 1-butanol phase 6.0 mg/ml
F: concentrated residue from defatted solution 2.0 mg/ml
G: purified *Gymnema inodorum* leaf extract 4.0 mg/ml
H: crude fraction I (11.0–31.5 min.) 1.0 mg/ml
I: crude fraction II (31.5–81.5 min.) 1.0 mg/ml
J: crude fraction III (81.5–140.0 min.) 1.0 mg/ml
d: peak 1 (d) component (31.5–33.5 min.) 0.5 mg/ml
e: peak 2 (e) component (33.5–37.0 min.) 0.5 mg/ml
f: peak 3 (f) component (43.0–47.0 min.) 0.5 mg/ml
g: peak 4 (g) component (53.0–58.5 min.) 0.5 mg/ml
h: peak 5 (h) component (60.0–66.0 min.) 0.5 mg/ml
i: peak 6 (i) component (67.5–73.0 min.) 0.5 mg/ml
j: peak 7 (j) component (77.0–81.5 min.) 0.5 mg/ml FIGS. 2 and 3 show analytical charts obtained by HPLC. Sample A unpurified *Gymnema inodorum* leaf extract was obtained without treating *Gymnema inodorum* leaves with acid.

As a result of the HPLC analysis, it has been confirmed that the preparation method of the present invention can efficiently decolor and purify the glucose absorption inhibiting substances contained in *Gymnema inodorum* leaves without damaging them, and that the glucose absorption inhibiting substances 1, 4, 6 and 7 and the glucose absorption inhibiting mixture containing them obtained by the method are purified to an extremely high degree. Peaks 1, 4, 6 and 7 obtained by the invention, which are the glucose absorption inhibiting substances, have been found to correspond to peaks d, g, i and j, respectively, in each analytical HPLC chart.

The properties of each of the peak 1, 4, 6 and 7 components were determined using the measuring equipment described above under the conditions described above. The results are as follows.

(1) Peak 1 Component
Compound name:
(3β, 4α, 16β)-16,23,28-trihydroxyolean-12-ene-3-yl-β-D-glucopyranuronic acid Chemical structure:

$C_{36}H_{58}O_{10}$ $R_1$:H
$R_2$:H

Melting point:

m.p.=203°–206° C.

UV:

λmax=223 nm

IR:

3400 (vs), 2950 (s), 1720 (s), 1620 (m), 1440 (m), 1350 (s), 1250 (m), 1160 (m), 1020 (vs) cm-

MS:

molecular weight=650 (m/z=649)

NMR:

TABLE 1

$^1$H Shift Coupling to the $^{13}$C Shift of Peak 1 Component (ppm)

| C-No. | Carbon Type | Chemical Shift | $^1$H Shift Coupling to the $^{13}$C Shift |
|---|---|---|---|
| [Aglycon moiety] | | | |
| 1 | —CH$_2$— | 39.6 | 0.95, 1.62 |
| 2 | —CH$_2$— | 26.3 | 1.74, 1.87 |
| 3 | >CH—O— | 83.3 | 3.63 |
| 4 | >C< | 43.9 | |
| 5 | >CH— | 48.1 | 1.26 |
| 6 | —CH$_2$— | 18.8 | 1.41, 1.53 |
| 7 | —CH$_2$— | 33.3 | 1.33, 1.71 |
| 8 | >C< | 41.1 | |
| 9 | >CH— | 48.2 | 1.62 |
| 10 | >C< | 37.5 | |
| 11 | —CH$_2$— | 24.7 | 1.91, 1.93 |
| 12 | —CH= | 123.9 | 5.24 |
| 13 | >C= | 144.3 | |
| 14 | >C< | 44.7 | |
| 15 | —CH$_2$— | 36.7 | 1.37, 1.83 |
| 16 | >CH—O— | 67.9 | 4.26 |
| 17 | >C< | 41.6 | |
| 18 | >CH— | 45.1 | 2.19 |
| 19 | —CH$_2$— | 47.9 | 1.05, 1.71 |
| 20 | >C< | 31.7 | |
| 21 | —CH$_2$— | 34.8 | 1.20, 1.42 |
| 22 | —CH$_2$— | 26.1 | 1.43, 2.13 |
| 23 | —CH$_2$—O— | 64.8 | 3.30, 3.62 |
| 24 | —CH$_3$ | 13.4 | 0.73 |
| 25 | —CH$_3$ | 16.6 | 1.01 |
| 26 | —CH$_3$ | 17.4 | 1.04 |
| 27 | —CH$_3$ | 27.5 | 1.26 |
| 28 | —CH$_2$—O— | 69.1 | 3.26, 3.86 |
| 29 | —CH$_3$ | 33.7 | 0.90 |
| 30 | —CH$_3$ | 24.3 | 0.93 |

TABLE 1-continued $^1$H Shift Coupling to the $^{13}$C Shift of Peak 1 Component (ppm)

| C-No. | Carbon Type | Chemical Shift | $^1$H Shift Coupling to the $^{13}$C Shift |
|---|---|---|---|
| [Glucopyranuronic acid moiety] | | | |
| 1' | —O—CH—O— | 105.9 | 4.46 |
| 2' | >CH—O— | 75.2 | 3.23 |
| 3' | >CH—O— | 77.8 | 3.37 |
| 4' | >CH—O— | 73.2 | 3.51 |
| 5' | >CH—O— | 76.5 | 3.79 |
| 6' | —COO— | 172.6 | |

(2) Peak 4 Component

Compound name:

(3β, 4α, 16β, 22α)-22-(N-methylanthraniloxy)-16,23,28-trihydroxyolean-12-ene-3-yl-3-O-β-D-glucopyranosyl-β-D-glucopyranuronic acid Melting point:

m.p.=218°–221° C.

UV:

λ max=233, 254, 355 nm

IR:

3350 (vs), 2925 (s), 1720 (m), 1650 (s), 1600 (m), 1570 (m), 1500 (m), 1350 (m), 1230 (s), 1020 (vs), 740 (m) cm-

MS:

molecular weight=961 (m/z=960)

NMR:

TABLE 2

$^1$H Shift Coupling to the $^{13}$C Shift of Peak 4 Component (ppm)

| C-No. | Carbon Type | Chemical Shift | $^1$H Shift Coupling to the $^{13}$C Shift |
|---|---|---|---|
| [Aglycon moiety] | | | |
| 1 | —CH$_2$— | 39.7 | |
| 2 | —CH$_2$— | 26.3 | 1.74, 1.94 |
| 3 | >CH—O— | 82.6 | near 3.6 |
| 4 | >C< | 44.0 | |

TABLE 2-continued

$^1$H Shift Coupling to the $^{13}$C Shift of Peak 4 Component (ppm)

| C-No. | Carbon Type | Chemical Shift | $^1$H Shift Coupling to the $^{13}$C Shift |
|---|---|---|---|
| 5 | >CH— | 48.1 | |
| 6 | —CH$_2$— | 18.9 | |
| 7 | —CH$_2$— | 33.3 | |
| 8 | >C< | 41.2 | |
| 9 | >CH— | 48.2 | 1.65 |
| 10 | >C< | 37.5 | |
| 11 | —CH$_2$— | 24.8 | near 1.97 |
| 12 | —CH= | 124.9 | 5.36 |
| 13 | >C= | 142.8 | |
| 14 | >C< | 44.0 | |
| 15 | —CH$_2$— | 37.0 | 1.40, 1.80 |
| 16 | >CH—O— | 66.9 | 4.70 |
| 17 | >C< | 46.5 | |
| 18 | >CH— | 44.9 | 2.58 |
| 19 | —CH$_2$— | 47.1 | 1.15, — |
| 20 | >C< | 33.0 | |
| 21 | —CH$_2$— | 39.9 | 1.66, — |
| 22 | >CH— | 74.4 | 5.63 |
| 23 | —CH$_2$—O— | 64.9 | 3.30, 3.64 |
| 24 | —CH$_3$ | 13.4 | 0.73 |
| 25 | —CH$_3$ | 16.7 | 1.02 |
| 26 | —CH$_3$ | 17.5 | 1.05 |
| 27 | —CH$_3$ | 28.0 | |
| 28 | —CH$_2$—O— | 61.3 | 3.59, 3.83 |
| 29 | —CH$_3$ | 33.5 | 1.00 |
| 30 | —CH$_3$ | 25.6 | 1.11 |

TABLE 3

$^1$H Shift Coupling to the $^{13}$C Shift of Peak 4 Component (ppm)

| C-No. | Carbon Type | Chemical Shift | $^1$H Shift Coupling to the $^{13}$C Shift |
|---|---|---|---|
| [Glucopyranuronic acid moiety] | | | |
| 1' | —O—CH—O— | 105.1 | 4.52 |
| 2' | >CH—O— | 74.4 | 3.45 |
| 3' | >CH—O— | 87.1 | 3.62 |
| 4' | >CH—O— | 71.6 | near 3.64 |
| 5' | >CH—O— | 75.7 | near 3.33 |
| 6' | —COO— | no data | |
| [Glucopyranose moiety] | | | |
| 1" | —O—CH—O— | 105.0 | 4.59 |
| 2" | >CH—O— | 74~78 | 3.28 |
| 3" | >CH—O— | 78.0 | 3.64 |
| 4" | >CH—O— | 71.6 | 3.6~3.7 |
| 5" | >CH—O— | 78.2 | 3.6~3.7 |
| 6" | —CH$_2$—O— | 62.6 | 3.89, 3.68 |
| [N-Methylanthranil moiety] | | | |
| A1 | >C=O | 169.6 | |
| A2 | >C= | 112.1 | |
| A3 | >C= | 153.0 | |
| A4 | —CH= | 111.9 | 6.68 |
| A5 | —CH= | 135.6 | 7.34 |
| A6 | —CH= | 115.3 | 6.55 |
| A7 | —CH= | 133.0 | 7.87 |
| N—Me | —CH$_3$ | 29.7 | 2.86 |

(3) Peak 6 Component

Compound name:

(3β, 4α, 16β,22α)-22-(N-methylanthraniloxy)-16,23,28-trihydroxyolean-12-ene-3-yl-β-D-glucopyranuronic acid Chemical structure:
C$_{44}$H$_{65}$O$_{12}$N

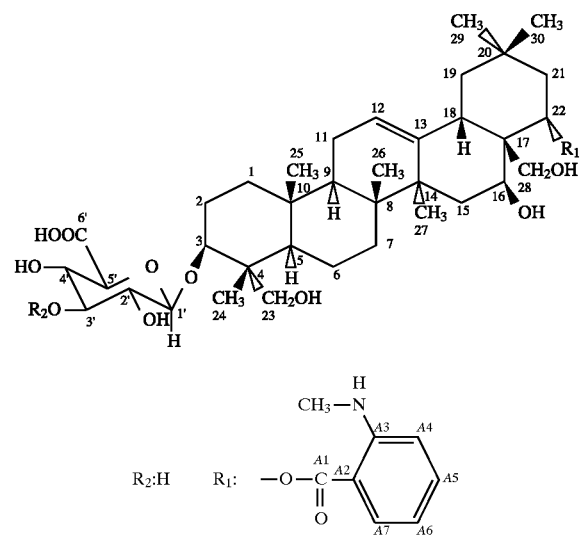

R$_2$:H    R$_1$: —O—C(=O)—(N-methylanthranil group)

Melting point:
m.p.=213°–216° C.
UV:
λ max=235, 254, 355 nm
IR:
3400 (vs), 2930 (s), 1730 (m), 1670 (s), 1610 (m), 1580 (m), 1520 (m), 1370 (m), 1240 (s), 1040 (vs), 750 (m) cm-
MS:
molecular weight=799 (m/z=798)
NMR:

TABLE 4

$^1$H Shift Coupling to the $^{13}$C Shift of Peak 6 Component (ppm)

| C-No. | Carbon Type | Chemical Shift | $^1$H Shift Coupling to the $^{13}$C Shift |
|---|---|---|---|
| [Aglycon moiety] | | | |
| 1 | —CH$_2$— | 39.7 | 1.62, 0.97 |
| 2 | —CH$_2$— | 26.2 | 1.92, 1.76 |
| 3 | >CH—O— | 82.3 | 3.67 |
| 4 | >C< | 43.9 | |
| 5 | >CH— | 48.1 | 1.28 |
| 6 | —CH$_2$— | 18.8 | 1.55, 1.42 |
| 7 | —CH$_2$— | 33.2 | 1.74, 1.34 |
| 8 | >C< | 41.2 | |
| 9 | >CH— | 48.2 | 1.64 |
| 10 | >C< | 37.5 | |
| 11 | —CH$_2$— | 24.8 | 1.92~2.03 |
| 12 | —CH= | 124.9 | 5.37 |
| 13 | >C= | 142.8 | |
| 14 | >C< | 43.9 | |
| 15 | —CH$_2$— | 37.0 | 1.78, 1.38 |
| 16 | >CH—O— | 66.8 | 4.71 |
| 17 | >C< | 46.5 | |
| 18 | >CH— | 44.9 | 2.58 |
| 19 | —CH$_2$— | 47.1 | 1.93, 1.13 |
| 20 | >C< | 33.0 | |
| 21 | —CH$_2$— | 39.9 | 1.80, 1.66 |
| 22 | >CH— | 74.3 | 5.63 |
| 23 | —CH$_2$—O— | 64.8 | 3.30, 3.64 |
| 24 | —CH$_3$ | 13.4 | 0.73 |
| 25 | —CH$_3$ | 16.7 | 1.02 |
| 26 | —CH$_3$ | 17.5 | 1.05 |

TABLE 4-continued

¹H Shift Coupling to the ¹³C Shift of Peak 6 Component (ppm)

| C-No. | Carbon Type | Chemical Shift | ¹H Shift Coupling to the ¹³C Shift |
|---|---|---|---|
| 27 | —CH$_3$ | 28.0 | 1.33 |
| 28 | —CH$_2$—O— | 61.2 | 3.83, 3.59 |
| 29 | —CH$_3$ | 33.5 | 0.99 |
| 30 | —CH$_3$ | 25.6 | 1.11 |

TABLE 5

¹H Shift Coupling to the ¹³C Shift of Peak 6 Component (ppm)

| C-No. | Carbon Type | Chemical Shift | ¹H Shift Coupling to the ¹³C Shift |
|---|---|---|---|
| [Glucopyranuronic acid moiety] | | | |
| 1' | —O—CH—O— | 105.3 | 4.46 |
| 2' | >CH—O— | 75.0 | 3.26 |
| 3' | >CH—O— | 78.0 | 3.41 |
| 4' | >CH—O— | 73.5 | 3.47 |
| 5' | >CH—O— | 76.6 | 3.70 |
| 6' | —COO— | no data | |
| [N-Methylanthranil moiety] | | | |
| A1 | >C=O | 169.6 | |
| A2 | >C= | 112.1 | |
| A3 | >C= | 153.0 | |
| A4 | —CH= | 111.9 | 6.68 |
| A5 | —CH= | 135.6 | 7.34 |
| A6 | —CH= | 115.3 | 6.55 |
| A7 | —CH= | 133.0 | 7.87 |
| N—Me | —CH$_3$ | 29.7 | 2.86 |

(4) Peak 7 Component
 Compound name:
  not designated
 Chemical structure:
  not decided (From UV and IR spectra, this compound is presumed to have an N-methylanthraniloxy group and thus to have a chemical structure similar to those of peak 4 and 6 components.)
 Melting point:
 m.p.=219° 221° C.
 UV:
 λ max=229, 254, 355 nm
 IR:
 3370 (vs), 2930 (s), 1720 (m), 1660 (s), 1610 (m), 1580 (m), 1510 (m), 1380 8m), 1240 (s), 1080 (vs), 740 (m) cm-
 MS:
 no data
 NMR:
 no data

EXAMPLE 2

Pretreatment/Decoloring Step with an Acid Solution

As described in Example 1, 10 liters of an aqueous acetic acid solution (pH 2.5) was added to 1 kg of dried and crushed *Gymnema inodorum* leaves and agitated at room temperature. The resultant mixture was treated in the same manner as described in Example 1 to thereby recover 708 g of acid-treated leaves.

Extraction Step

To 400 g of the above acid-treated leaves, 4 liters of aqueous 75% ethanol solution was added and agitated at room temperature. After 1 hour, the mixture was vacuum filtered using a quantitative filter paper No. 5A (Toyo) to thereby obtain an extract. To the acid-treated leaf cake, 4 liters of aqueous 75% ethanol solution was added again, extracted under agitation for 1 hour at room temperature and then filtered similarly to thereby obtain an extract. Both extracts were mixed to thereby obtain about 8 liters of extract.

Concentration Step

The thus obtained extract was concentrated under reduced pressure in a rotary evaporator under 30 mmHg at 80° C. until the smell of ethanol was eliminated. As a result, 1.1 liters of a concentrate was obtained. Of this concentrate, 100 ml was further concentrated and dried/caked to thereby obtain 3.8 g of light brown, roughly purified *Gymnema inodorum* leaf extract. To the remaining 1 liter of the concentrate, water was added to make the total volume 3 liters.

Partition Extraction Step

The thus prepared 3 liter concentrate was treated as described in Example 1 to thereby obtain about 1.8 liters of 1-butanol solution.

Defatting/Decoloring Step

To the resultant 1-butanol solution, 80 g of celite was added, and then treated as described in Example 1, to thereby obtain 117.8 g of fine powder of which the excipient was celite. Two liters of diethyl ether was added thereto. The mixture was defatted twice in the same manner as described in Example 1 to thereby obtain 100.9 g of fine powder of which the excipient is celite.

Purification with a Highly Polar Solvent

The defatted fine powder (100.9 g) was treated as described in Example 1 to thereby obtain 19.8 g of light yellow-green, purified *Gymnema inodorum* leaf extract.

Isolation and Purification by Preparative HPLC 17.4 g of the thus obtained light yellow-green, purified *Gymnema inodorum* leaf extract was applied to preparative HPLC in the same manner as described in Example 1 to thereby obtain crude fraction II from 31.5–81.5 min. containing four glucose absorption inhibiting substances. Further, a fraction from 31.5–33.5 min. (peak 1 component), a fraction from 53.0–58.5 min. (peak 4 component), a fraction from 67.5–73.0 min. (peak 6 component), and a fraction from 77.0–81.5 min. (peak 7 component) were obtained which are the above-mentioned four glucose absorption inhibiting substances. Then, each of the fraction solutions obtained was concentrated under reduced pressure using a rotary evaporator under 30 mmHg at 80° C. until the smell of acetonitrile was eliminated. The resultant concentrate was subjected to liquid—liquid partition extraction using 1-butanol. The 1-butanol phase was concentrated and dried/caked in a rotary evaporator under 30–5 mmHg at 80° C. The resultant cake was further dried in a vacuum drier at 80° C. for 16 hours.

Figure 4:
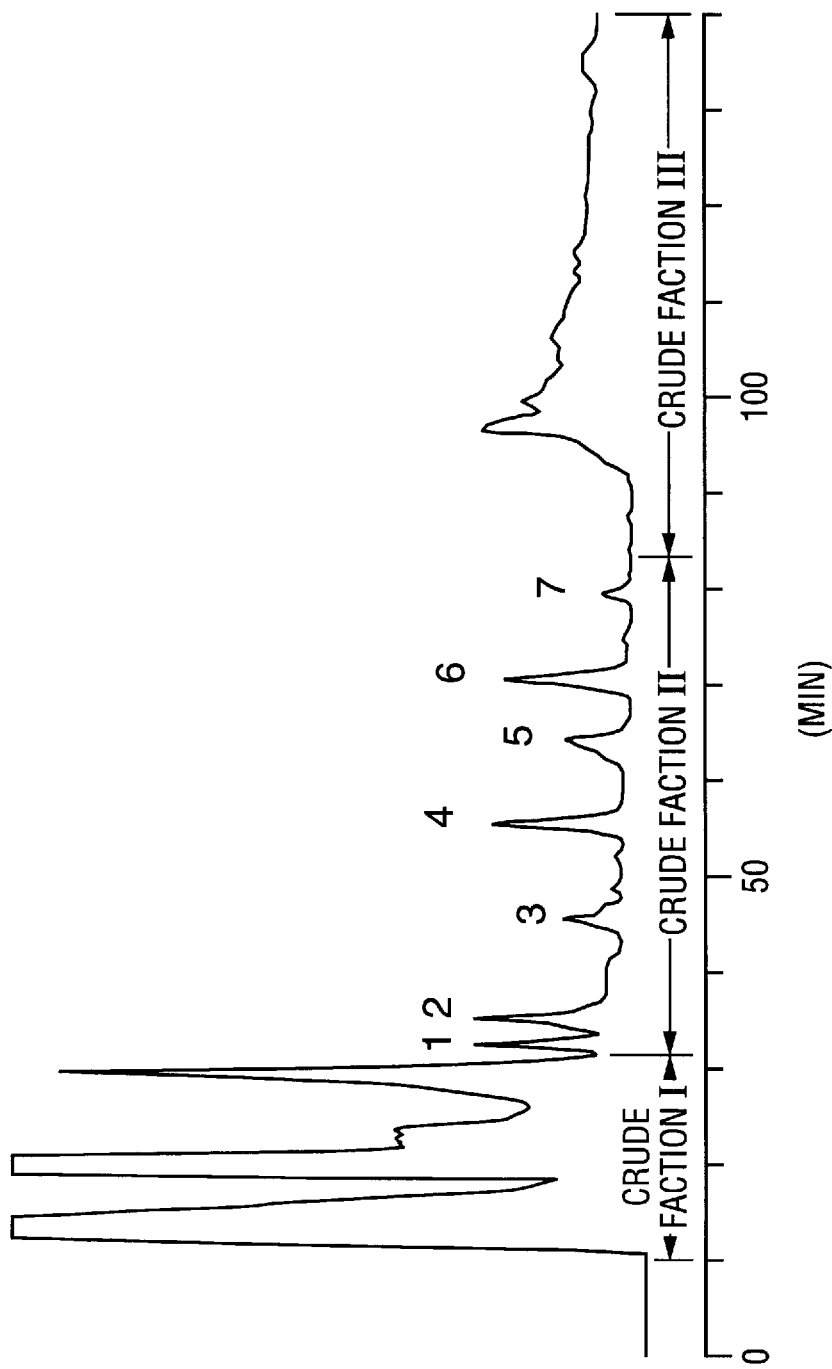
FIG. 4 is a preparative HPLC chart of peak 1, peak 4, peak 6 and peak 7 components in crude fraction II in Example 2.

The preparative time and yield of each fraction were as follows:

31.5–33.5 min.: peak 1 component 185 mg
53.0–58.5 min.: peak 4 component 80 mg
67.5–73.0 min.: peak 6 component 60 mg
77.0–81.5 min.: peak 7 component 63 mg
31.5–81.5 min.: crude fraction II 510 mg The preparative HPLC fraction chart is given in FIG. 4.

Recrystallization

The thus obtained each fraction was recrystallized in the same manner as described in Example 1 to thereby obtain colorless or light yellow crystals of each fraction.

Figure 5:
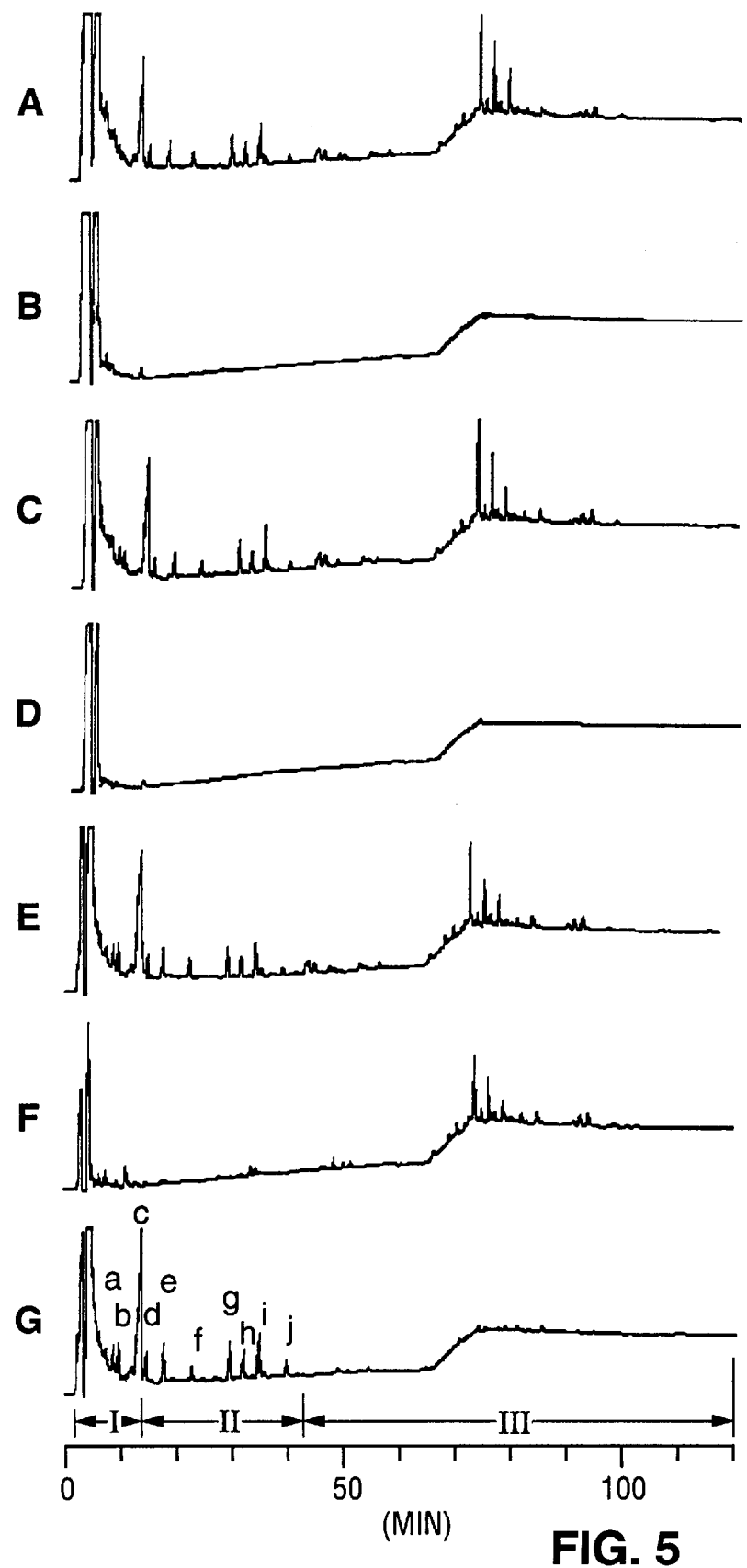
FIG. 5 shows HPLC charts of an unpurified extract from *Gymnema inodorum* leaves (A) and the following materials obtained in Example 2: the concentrated residue from acid-treated solution (B); the roughly purified *Gymnema inodorum* leaf extract (C); the concentrated residue from partition aqueous phase (D); the concentrated residue from partition 1-butanol phase (E); the defatted components (F); and the purified *Gymnema inodorum* leaf extract (G).
Figure 6:
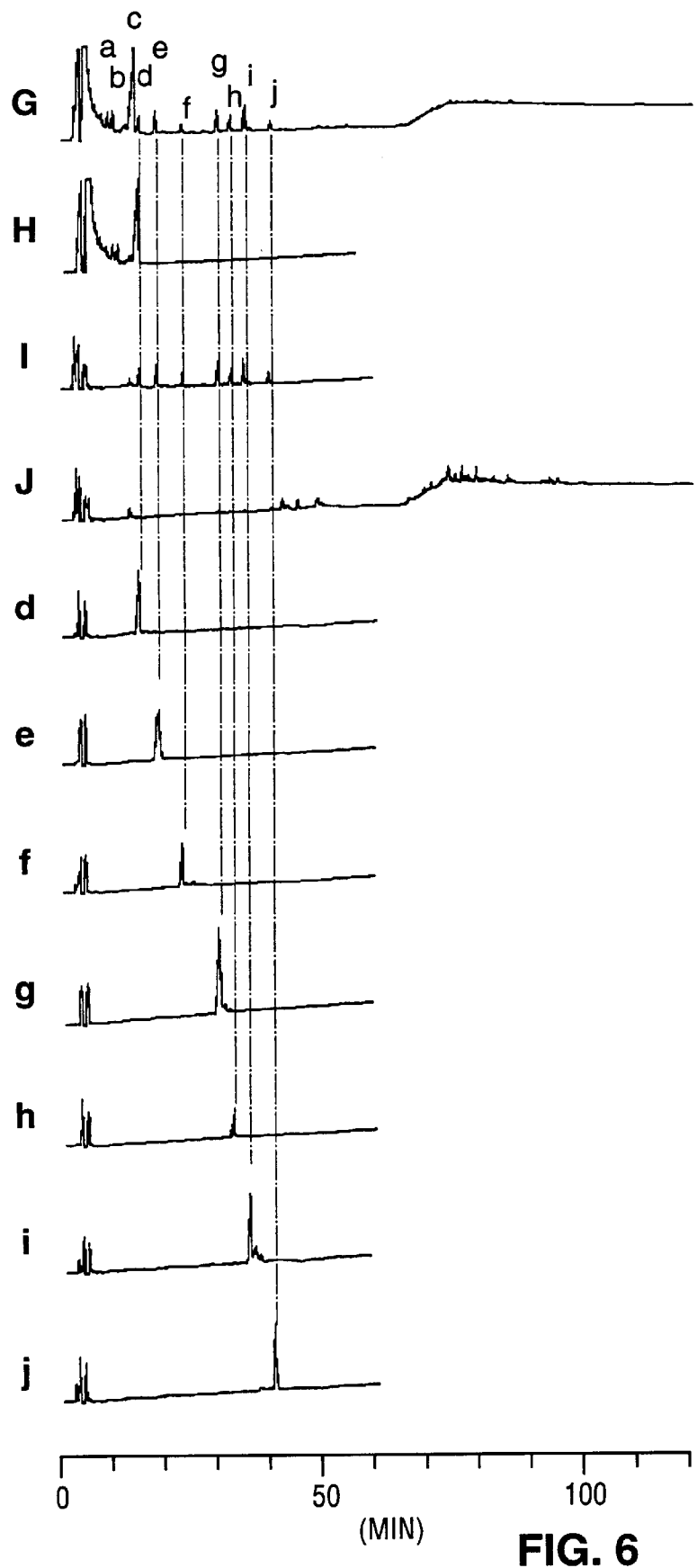
FIG. 6 shows HPLC charts of the following materials obtained in Example 2: the purified *Gymnema inodorum* leaf extract (G); crude fraction I (H); crude fraction II (I); crude fraction III (J); peak 1 component (d); peak 2 component (e); peak 3 component (f); peak 4 component (g); peak 5 component (h); peak 6 component (i); and peak 7 component (j).

The yields of those crystals were as follows.
(Yields after recrystallization)
Peak 1 110 mg
Peak 4 61 mg
Peak 6 46 mg
Peak 7 48 mg
Crude fraction II 256 mg The state of separation and purification of the products obtained from individual purification steps and the crystals obtained from each fraction in Example 2 were analyzed by HPLC in the same manner as described in Example 1. Analytical charts by HPLC are shown in FIGS. 5 and 6.

As a result of the HPLC analysis, it has been confirmed, as in the case of Example 1, that the preparation method of the present invention can efficiently decolor and purify the glucose absorption inhibiting substances contained in *Gymnema inodorum* leaves without damaging them, and that the glucose absorption inhibiting substances 1, 4, 6 and 7 and the glucose absorption inhibiting mixture containing them obtained by the method are purified to an extremely high degree.

The properties of each of the above-mentioned fractions were also measured as described in Example 1. As a result, for each of the fractions of Example 1, the same results as obtained for the corresponding fraction of Example 1 have been obtained. Accordingly, the peak 1, 4, 6 and 7 components of Example 2 have been confirmed to be identical with the peak 1, 4, 6 and 7 components of Example 1, respectively.

Hereinbelow, the results of a glucose tolerance test will be shown on each of the products from preparation steps, each glucose absorption inhibiting substance and glucose absorption inhibiting mixture of the invention together with the results on those crude fractions and peaks which do not have glucose absorption inhibiting action. The "peak 1 component", "peak 4 component", "peak 6 component" and "peak 7 component" as used in the following glucose tolerance test refer to the compounds obtained in Example 1.

The details of the method for the glucose tolerance test were as follows.

(Method of the glucose tolerance test)
Dilution medium for test samples:
0.5% CMC-Na suspension
Test animals:
7-Week old male SD rats (purchased from Nippon S.L.C.) were used after one-week preparatory breeding in which the rats were fed with a solid feed (F-2 for feeding mouse/rat) and water in a breeding chamber at 23°–26° C. under a humidity of 50–60%.
Dose of test samples:
Each of the products from purification steps, the roughly purified *Gymnema inodorum* leaf extract and the purified *Gymnema inodorum* leaf extract obtained in Example 1, and reference materials (unpurified *Gymnema inodorum* leaf extract and *Gymnema inodorum* leaf-containing components) were administered as follows:
A: unpurified *Gymnema inodorum* leaf extract 800 mg/kg
B: concentrated residue from acid-treated solution 400 mg/kg
C: roughly purified *Gymnema inodorum* leaf extract 400 mg/kg
D: concentrated residue from partition aqueous phase 400 mg/kg
E: concentrated residue from partition 1-butanol phase 400 mg/kg
F: defatted components 200 mg/kg
G: purified *Gymnema inodorum* leaf extract 200 mg/kg
H: crude fraction I in FIG. 1 260 mg/kg
I: crude fraction II in FIG. 1 60 mg/kg
J: crude fraction III in FIG. 1 80 mg/kg
d: peak 1 component in FIG. 1 30 mg/kg
e: peak 2 component in FIG. 1. 30 mg/kg
f: peak 3 component in FIG. 1 30 mg/kg
g: peak 4 component in FIG. 1 30 mg/kg
h: peak 5 component in FIG. 1 30 mg/kg
i: peak 6 component in FIG. 1 30 mg/kg
j: peak 7 component in FIG. 1 30 mg/kg
Dose of sugar:
glucose 1,000 mg/kg
Preparation of the sample and the sugar:
Each of the test samples was appropriately diluted with the above-mentioned medium to thereby prepare a suspension. As the sugar to be administered, an aqueous glucose solution was prepared at a concentration of 100 mg/ml.
Administration of the test sample and the sugar:
The sample and the glucose solution were administered orally to rats compulsorily using an oral sound. The control group was administered the medium and the glucose solution.
Volume of administration:
The test sample was administered at a dose of 2 ml/kg and the aqueous glucose solution was administered at a dose of 10 ml/kg.
Glucose tolerance test:
5 rats weighing 250–265 g after undergoing a fast of 16 hours (free access to water was allowed) were used as one group. One hour after the removal of the water container from each cage, blood samples were collected from rats and the blood sugar level was determined for each sample. Rats were selected so that average blood sugar values in individual groups were equal. Then, the test sample was administered and, immediately after that, glucose was administered orally. 15, 30, 60 and 120 minutes after the glucose loading, a blood sample was collected from each rat. Each time, a sample was taken from the tail vein by 50 $\mu$l, mixed with 50$\mu$l of 10 mg/ml sodium fluoride (dissolved in saline) and then used for determination. The blood sugar level in whole blood was determined using an automatic glucose determination apparatus (Model GA-1120 manufactured by Kyoto Daiichi Kagaku).
Statistical analysis:
The results of the test were shown in average values. Average values and standard errors were calculated, and the significant difference between the control group and each treatment group was tested. Dunnett's multiple comparison test was used as a test method and the significant level was set at less than 5% in the ratio of risk.

Figure 7:
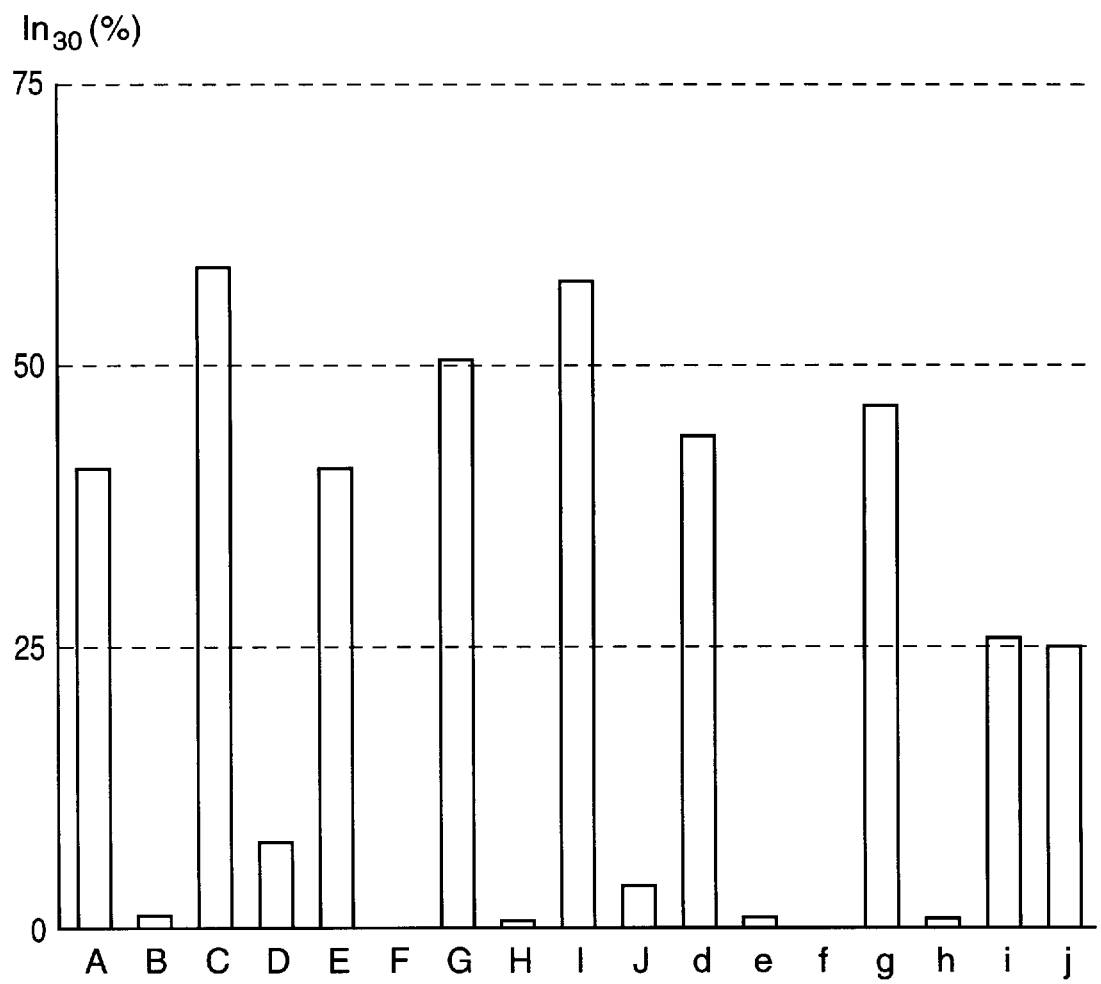
FIG. 7 shows the results of a glucose tolerance test. More specifically, this Figure shows blood sugar increase inhibition ratios 30 minutes after glucose loading of an unpurified *Gymnema inodorum* leaf extract (A) and the following materials obtained in Example 1: the concentrated residue from acid-treated solution (B); the roughly purified *Gymnema inodorum* leaf extract (C); the concentrated residue from partition aqueous phase (D); the concentrated residue from partition 1-butanol phase (E); the defatted components (F); the purified *Gymnema inodorum* leaf extract (G); crude fraction II (I); crude fraction III (J); peak 1 component (d); peak 2 component (e); peak 3 component (f); peak 4 component (g); peak 5 component (h); peak 6 component (i); and peak 7 component (j).

The results are shown in Table 6 and FIG. 7.
In FIG. 7, the values of $In_{30}$ (%) were calculated by the following formula:

$$In_{30}\ (\%)=100-[(Bi_{30}-Bi_0)/(Bc_{30}-Bc_0)]\times 100$$

wherein $In_{30}$ (%): blood sugar increase inhibiting ratio (%) 30 minutes after the glucose loading;
$Bi_{30}$: blood sugar level (mg/dl) in a test sample 30 minutes after the glucose loading;

$Bi_0$: blood sugar level (mg/dl) in a test sample before the glucose loading;

$Bc_{30}$: blood sugar level (mg/dl) in the control group 30 minutes after the glucose loading; and $Bc_0$: blood sugar level (mg/dl) in the control group before the glucose loading.

TABLE 6

| Test substance | Dose (mg/kg, p.o.) | Blood Sugar Level (mg/dl) Minutes after Glucose | | | | |
|---|---|---|---|---|---|---|
| | | Before loading | 15 | 30 | 60 | 120 |
| Control group | — | 63 ± 1 | 118 ± 8 | 136 ± 4 | 112 ± 2 | 81 ± 3 |
| A. Unpurified extract | 800 | 64 ± 1 | 96 ± 3* | 107 ± 3* | 93 ± 2* | 89 ± 3 |
| B. Concentrated residue from acid-treated solution | 400 | 63 ± 2 | 119 ± 3 | 135 ± 5 | 114 ± 3 | 84 ± 2 |
| C. Roughly purified extract | 400 | 64 ± 2 | 85 ± 3* | 94 ± 1* | 102 ± 2* | 93 ± 1 |
| D. Partition aqueous phase | 400 | 66 ± 3 | 123 ± 5 | 131 ± 5 | 109 ± 3 | 87 ± 3 |
| E. 1-Butanol phase | 400 | 64 ± 3 | 92 ± 4* | 107 ± 3* | 116 ± 6 | 106 ± 6 |
| F. Defatted components | 200 | 65 ± 3 | 114 ± 2 | 138 ± 3 | 116 ± 4 | 88 ± 2 |
| G. Purified extract | 200 | 64 ± 3 | 92 ± 5* | 100 ± 2* | 93 ± 4* | 90 ± 3 |
| H. Crude fraction I | 260 | 63 ± 2 | 112 ± 2 | 135 ± 7 | 106 ± 4 | 78 ± 2 |
| I. Crude fraction II | 60 | 63 ± 2 | 81 ± 2* | 94 ± 4* | 102 ± 5 | 90 ± 2 |
| J. Crude fraction III | 80 | 67 ± 2 | 113 ± 5 | 137 ± 4 | 112 ± 7 | 83 ± 2 |
| d. d component crystal | 30 | 63 ± 1 | 88 ± 3* | 104 ± 3* | 112 ± 4 | 90 ± 2 |
| e. e component crystal | 30 | 66 ± 2 | 121 ± 4 | 138 ± 5 | 114 ± 3 | 84 ± 1 |
| f. f component crystal | 30 | 66 ± 2 | 124 ± 3 | 139 ± 3 | 111 ± 2 | 82 ± 1 |
| g. g component crystal | 30 | 62 ± 1 | 97 ± 4* | 101 ± 5* | 96 ± 3 | 82 ± 3 |
| h. h component crystal | 30 | 64 ± 2 | 114 ± 4 | 136 ± 4 | 119 ± 3 | 82 ± 2 |
| i. i component crystal | 30 | 66 ± 2 | 99 ± 1* | 120 ± 3* | 106 ± 4 | 84 ± 1 |
| j. j component crystal | 30 | 64 ± 3 | 101 ± 6* | 119 ± 4* | 119 ± 2 | 94 ± 3 |

Mark "*" indicates that there is a significant difference (p < 0.05) in the statistical analysis.

While the roughly purified *Gymnema inodorum* leaf extract, the concentrated residue from 1-butanol phase and the purified *Gymnema inodorum* leaf extract exhibited a blood sugar increase inhibiting action equivalent to that of the unpurified *Gymnema inodorum* leaf extract at a dose ¼–½ of that of the unpurified extract, the concentrated residue from the acid-treated solution, the concentrated residue from partition aqueous phase and the defatted components revealed no blood sugar increase inhibiting action. Accordingly, the preparation method of the invention has been found to be able to efficiently decolor and purify the glucose absorption inhibiting substances in *Gymnema inodorum* leaves without damaging them. In addition, crude fraction II containing the four glucose absorption inhibiting substances obtainable from preparative HPLC of the purified *Gymnema inodorum* leaf extract revealed a significant blood sugar increase inhibiting action in an extremely small amount. Further, the compounds represented by the general formula (I) described above comprising the four components of peaks 1, 4, 6 and 7 isolated from *Gymnema inodorum* leaves revealed a significant blood sugar increase inhibiting action in an extremely small amount.

EFFECT OF THE INVENTION

According to the present invention, it is possible to efficiently concentrate and purify the glucose absorption inhibiting substances contained in *Gymnema inodorum* leaves. The four glucose absorption inhibiting substances and the glucose absorption inhibiting mixture comprising at least one of them obtained by the invention are able to reveal glucose absorption inhibiting action in intestinal tracts even in an extremely small amount. Also, a food or drink or an additive to food or drink obtained by adding thereto the above substance(s) or mixture can reveal dietary effects and diabetes-preventive effects without its inherent color being spoiled, since the substance(s) and the mixture have a light color. Furthermore, in the present invention, the four glucose absorption inhibiting substances contained in *Gymnema inodorum* leaves have been isolated and they have been confirmed to correspond to peaks d, g, i and j in analytical HPLC charts. Their chemical structures have also been specified in the invention. Accordingly, it has become possible to qualitatively and quantitatively analyze the above substances in a food or drink by HPLC or the like. Thus, it is possible to examine whether those substances have been degraded or not during the processing step of the food or drink by heat, light and chemicals such as acid and alkali. The problem of quality control has been solved.

What is claimed is:

1. A (3β,4α,16β)-16,23,28-trihydroxyolean-12-ene-3-yl-β-D-glucopyranuronic acid derivative represented by the general formula (I):

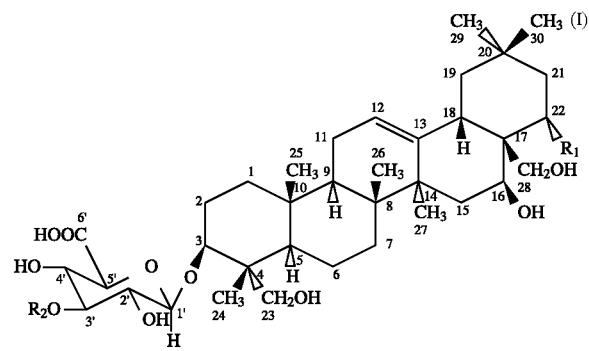

wherein $R_1$ is a hydrogen atom or a group represented by the following formula:

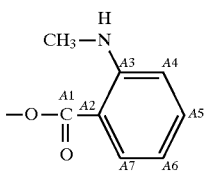

and $R_2$ is a hydrogen atom or a group represented by the following formula:

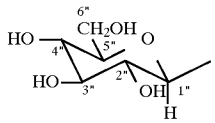

2. (3β, 4α, 16β)-16,23,28-trihydroxyolean-12-ene-3-yl-β-D-glucopyranuronic acid.

3. ( 3β, 4α, 16β, 22α) -22-(N-methylanthraniloxy)-16 ,23 ,28-trihydroxyolean-12-ene-3-yl-3-O-β-D-glucopyranosyl-β-D-glucopyranuronic acid.

4. (3β, 4α, 16β,22α)-22-(N-methylanthraniloxy)-16,23, 28-trihydroxyolean-12-ene-3-yl-β-D-glucopyranuronic acid.

5. A method for preparing the (3β,4α, 16β)-16,23,28-trihydroxyolean-12-ene-3-yl-β-D-glucopyranuronic acid derivative represented by the general formula (I) of claim 1, comprising:

treating *Gymnema inodorum* leaves with an aqueous acid solution;

dehydrating and washing the leaves;

extracting the leaves with a lower alcohol and/or water;

concentrating the resultant extract under reduced pressure;

subjecting the resultant concentrate to a liquid—liquid partition extraction with water and 1-butanol;

adding an excipient to the resultant 1-butanol phase and then concentrating and drying/caking the phase under reduced pressure;

then washing the resultant cake with an organic solvent to defat the cake;

extracting the resultant defatted cake with a highly polar solvent;

concentrating and drying/caking the resultant extract to thereby obtain a purified *Gymnema inodorum* leaf extract; and subjecting the resultant extract to a preparative high performance liquid chromatography (HPLC) of a reversed phase partition system using as a stationary phase an octadecyl group-bound silica gel under the following conditions:

[Conditions in preparative HPLC]

Preparative column:

TSKgel ODS-80T$_M$ (reversed-phase partition system/ Tosoh Corp.)

Column size: 21.5 mm I.D.×30 cm

Eluent:

Solution A Acetonitrile:distilled water:acetic acid =50.0:50.0:0.1 (v/v%)

Solution B Acetonitrile:distilled water:acetic acid =55.2:44.8:0.1 (v/v%)

Solution C Acetonitrile:distilled water:acetic acid =90.0:10.0:0.1 (v/v%)

Gradient:

0→78 min. A→B linear gradient

78→83 min. B→C linear gradient

83→140 min. isocratic elution with Solution C

Flow rate:

6.0 ml/min.

Detector:

Ultraviolet-visible detector (210 nm)

Column temperature:

40° C.

to thereby obtain colorless or light yellow fractions which are obtained as fractions from 31.5–33.5 min., 53.0–58.5 min., 67.5–73.0 min. and 77.0–81.5 min.

6. A glucose absorption inhibiting composition comprising at least one (3β, 4α, 16β)-16,23,28-trihydroxyolean-12-ene-3-yl-β-D-glucopyranuronic acid derivative represented by the general formula (I) of claim 1.

7. A food or drink additive comprising at least one (3β, 4α, 16β)-16,23,28-trihydroxyolean-12-ene-3-yl-β-D-glucopyranuronic acid derivative represented by the general formula (I) of claim 1.

8. A dietary food or drink comprising at least one (3β, 4α, 16β)-16, 23,28-trihydroxyolean-12-ene-3-yl-β-D-glucopyranuronic acid derivative represented by the general formula (I) of claim 1.

9. A diabetes-preventive food or drink comprising at least one (3 β,4α, 16 β)-16,23,28-trihydroxyolean-12-ene-3-yl-β-D-glucopyranuronic acid derivative represented by the general formula (I) of claim 1.

* * * * *